(12) United States Patent
Rhine-Pallas et al.

(10) Patent No.: US 8,930,222 B2
(45) Date of Patent: Jan. 6, 2015

(54) METHOD AND SYSTEM FOR MANAGING PATIENT HEALTHCARE

(75) Inventors: Amy L. Rhine-Pallas, Chicago, IL (US); Robert J. Padley, Lake Bluff, IL (US); Brett M. Hickman, New Palestine, IN (US); Clifford Bleustein, New York, NY (US); Refaat A. Hegazi, Dublin, OH (US); Sudarshan Hebbar, Kansas City, MO (US); David K. Spindell, Coral Springs, FL (US); Paul Audhya, Dallas, TX (US)

(73) Assignee: Abbott Laboratories, Abbott Park, IL (US)

( * ) Notice: Subject to any disclaimer, the term of this patent is extended or adjusted under 35 U.S.C. 154(b) by 351 days.

(21) Appl. No.: 13/204,125

(22) Filed: Aug. 5, 2011

(65) Prior Publication Data
US 2012/0035958 A1 Feb. 9, 2012

Related U.S. Application Data

(60) Provisional application No. 61/371,058, filed on Aug. 5, 2010.

(51) Int. Cl.
*G06F 19/00* (2011.01)
*G06Q 50/24* (2012.01)
(52) U.S. Cl.
CPC ........ *G06F 19/3456* (2013.01); *G06F 19/3431* (2013.01); *G06F 19/3443* (2013.01); *G06Q 50/24* (2013.01)
USPC ............................................................ 705/3

(58) Field of Classification Search
USPC ............ 705/2, 3; 600/410; 435/7.1; 514/170
See application file for complete search history.

(56) References Cited

U.S. PATENT DOCUMENTS

| 6,385,589 | B1 | 5/2002 | Trusheim et al. | |
|---|---|---|---|---|
| 6,612,985 | B2 | 9/2003 | Eiffert et al. | |
| 6,802,810 | B2 | 10/2004 | Ciarniello et al. | |
| 2001/0037215 | A1 | 11/2001 | Sparks | |
| 2002/0010597 | A1* | 1/2002 | Mayer et al. ...................... | 705/2 |
| 2002/0022236 | A1* | 2/2002 | Comper ......................... | 435/7.1 |
| 2003/0046113 | A1* | 3/2003 | Johnson et al. ..................... | 705/3 |
| 2005/0197561 | A1* | 9/2005 | Elsinger et al. ............... | 600/410 |
| 2007/0122824 | A1 | 5/2007 | Tucker et al. | |
| 2008/0070879 | A1* | 3/2008 | Sageman et al. .............. | 514/170 |

(Continued)

FOREIGN PATENT DOCUMENTS

WO WO 2008/127918 A1 10/2008

OTHER PUBLICATIONS

"Criteria for diagnosis, staging, risk stratification and response assessment of multiple myeloma"; Kyle et al.; Leukemia; Jan. 2009.*

(Continued)

*Primary Examiner* — John Pauls
(74) *Attorney, Agent, or Firm* — Baker Botts L.L.P.

(57) ABSTRACT

Methods and systems are provided for managing patient healthcare, which include creating a patient profile for a patient, screening and assessing the patient with respect to a disease and updating the patient profile, determining a health management status of the patient with respect to the disease based on a comparison of the updated patient profile to at least one predefined criterion regarding progression of the disease, and providing a recommended action based upon the health management status and updated patient profile.

35 Claims, 5 Drawing Sheets

(56) References Cited

U.S. PATENT DOCUMENTS

| | | | |
|---|---|---|---|
| 2009/0083075 A1 | 3/2009 | Henschke et al. | |
| 2009/0089088 A1* | 4/2009 | Schoenberg | 705/2 |
| 2009/0228304 A1 | 9/2009 | Ciarniello et al. | |

OTHER PUBLICATIONS

"New Interantional Staging System for Lung Cancer"; Mountain; Chest; Apr. 1966.*

"Staging of brain pathology related to sporadic Parkinson's disease" Braak et al.; Neurobiology of Aging; 2003.*

International Search Report and Written Opinion for PCT/US2011/046762 dated Nov. 3, 2011.

Adams, et al., "Guidelines for the Early Management of Adults with Ischemic Stroke: A Guideline from the American Heart Association/American Stroke Association Stroke council, Clinical Cardiology Council, Cardiovascular Radiology and Intervention Council, and the Atherosclerotic Peripheral Vascular Disease and Quality of Care Outcomes in Research Interdisciplinary Working Groups: The American Academy of Neurology Affirms the value of this guideline as an educational tool for neurologists", *Circulation*, 115-e478-e534 (2007).

American Diabetes Association, "Living with Diabetes", *Treatment & Care*, available http://www.diabetes.org/living-with-diabetes/treatment-and-care (2009) [Retrieved on Oct. 31, 2013].

American Diabetes Association, "Standards of Medical Care in Diabetes", *Diabetes Care*, 32(S1): S13-S61 (2009).

American Heart Association, "ACC/AHA 2005 Guidelines for the Management of Patients with Peripheral Arterial Disease (Lower Extremity, Renal, Mesenteric, and Abdominal Aortic): Executive Summary", *Journal of the American College of Cardiology*, 47(6):1-75 (2006).

American Heart Association, "2009 Focused Update Incorporated Into the ACC/AHA 2005 Guidelines for the Diagnosis and Management of Heart Failure in Adults: A Report of the American College of Cardiology Foundation/American Heart Association Task Force on Practice Guidelines: Developed in Collaboration with the International Society for Heart and Lung Transplantation", *Circulation*, 119: e391-e479 (2009).

Kavey, et al., "American Heart Association Guidelines for Primary Prevention of Atherosclerotic Cardiovascular Disease beginning in Childhood", *Circulation*, 107-1562-1566 (2003).

Lauer, "Primary Prevention of Atherosclerotic Cardiovascular Disease: The high Public Burden of Low Individual Risk", *JAMA*, 297(12):1376-1378 (2007).

Pearson, et al., "AHA Guidelines for Primary Prevention of Cardiovascular Disease and Stroke: 2002 Update: Consensus Panel Guide to Comprehensive Risk Reduction for Adult Patients Without Coronary or Other Atherosclerotic Vascular Diseases", *Circulation*, 106-388-391 (2002).

Smith, et al., "AHA/ACC Guidelines for Secondary Prevention for Patients with Coronary and Other Atherosclerotic Vascular Disease: 2006 Update: Endorsed by the National Heart, Lung, and Blood Institute", *Circulation*, 113:2363-2372 (2006).

Zeeuw, et al., "Microalbuminuria as an Early Marker for Cardiovascular Disease", *Journal of American Society of Nephrology*, 14: 2100-2105 (2006).

United States Preventive Services Task Force Clinical Preventive Services Pocket Guide, pp. 3-10 (2009).

Department of Health (UK), "Five Years on Delivering the Diabetes National Service Framework", pp. 1-44 (2008).

* cited by examiner

METHOD AND SYSTEM FOR MANAGING PATIENT HEALTHCARE

CROSS-REFERENCE TO RELATED APPLICATIONS

This application claims priority, under 35 U.S.C. §119(e), to U.S. Provisional Patent Application Ser. No. 61/371,058, filed Aug. 5, 2010, the disclosure of which is incorporated herein by reference in its entirety.

FIELD OF THE INVENTION

The presently disclosed subject matter relates to systems and methods for managing patient care. More particularly, the disclosed subject matter relates to a comprehensive healthcare management system for screening patients for one or more diseases, assessing patients' healthcare status, and providing recommended actions to address the diseases.

BACKGROUND OF THE INVENTION

In the United States, cardiovascular disease (including, e.g., heart disease and stroke), cancer, and diabetes are among the leading causes of death. Based on available data for 2006, it is estimated that nearly one million Americans die of cardiovascular disease each year, which is about 40% of all deaths. One out of every four Americans has cardiovascular disease. Heart disease and stroke account for almost 6 million hospitalizations each year and cause disability for almost 10 million Americans age 65 years and older. Meanwhile, it is estimated that a total of 23.6 million children and adults in the United States (7.8% of the population) have diabetes according to the available data for 2007. Among these, 17.9 million were diagnosed with diabetes, 5.7 million people were undiagnosed. In addition, 57 million people are pre-diabetes, and 1.6 million new cases of diabetes are diagnosed in people aged 20 years and older each year. Among people age 20 years or older, 23.5 million (or 10.7% of all people in this age group) have diabetes. People with diabetes are also at significantly increased risk of cardiovascular diseases.

Although these diseases remain difficult to completely prevent or treat, early detection and proper medical intervention are important to reduce the risk of the diseases, slow the progression of the diseases, alleviate the suffering of patients, and improve quality of life.

Regarding these and other diseases, the currently available healthcare systems are facing multitude of challenges. One of the challenges concerns healthcare quality. The failure to detect, diagnose or treat heart diseases is still one of the leading reasons for heart failure. Further, the failure to identify preferred therapy can result in a lapse of optimal healthcare. Although a variety of guidelines are available from different professional associations, there is no unified approach to capture the benefits of these independent sources.

Another challenge for the current healthcare systems arises from ineffective communication across the various practices or healthcare providers involved in the diagnosis, treatment, and/or prevention of a particular disease. This inability to effectively and efficiently communicate between practices and healthcare providers is further exacerbated when attempting to address two or more diseases correlated by co-morbidity. Individual care is delivered in numerous different locations by individuals and organizations that are often unrelated. Therefore, critical patient data may be dispersed in many different locations and often in incompatible formats, and can be difficult to obtain on the point of care. This fragmentation of patient information accounts for many of the inefficiencies and lapses in patient care, which can lead to medical mistakes and excess costs.

Yet another challenge for the healthcare system is the escalating costs. Expenditures in the United States on health care surpassed $2.3 trillion in 2008, which is was about $7,681 per resident and accounts for 16.2% of the nation's Gross Domestic Product (GDP). These expenditures are more than three times the $714 billion spent in 1990, and over eight times the $253 billion spent in 1980. Stemming this growth has become a major policy priority, as the government, employers, and consumers increasingly struggle to keep up with healthcare costs.

There is a need for patient healthcare management systems and methods for improving communication and access to relevant information and data to thus improve the overall outcome of patient healthcare, which provide individuals or parties involved in healthcare with information and tools to facilitate the diagnosis and treatment of patients and to improve the quality and cost of patient healthcare.

SUMMARY

In accordance with one aspect of the disclosed subject matter, a method of managing patient healthcare is provided. First, a patient profile is created, which includes patient data for a patient. The patient is then screened for a disease based on the patient profile. Thereafter, at least one test is identified to assess a state of the disease based on the patient profile, and the state of the disease is assessed based upon results of the test. The patient profile is updated accordingly to include the results of the at least one test and the assessed disease state. Based on a comparison of the updated patient profile to at least one predefined criterion regarding progression of the disease, a health management status of the patient with respect to the disease is determined. In certain embodiments, the health management status of the patient includes different stages of progression of the disease. A recommended action is then provided, and implemented to address the disease.

In certain embodiments, the screening is selected based on the patient data. The disease for screening can be either selected from diseases the patient is prone to have based on the patient profile, or pre-selected. The screening can be performed by questions, inspecting historical health records of the patients, etc. In specific embodiments, the screening is based on professional guidelines relating to the disease. The professional guidelines can include, for example, guidelines published by the American Heart Association, American College of Cardiology, American Stroke Association, and American Diabetes Association. The test for assessing the state of the disease identified in the screening includes diagnostic tests, such as lab tests or physical examinations. The diagnostic test can be selected according to professional guidelines relating to the disease.

Certain embodiments of the disclosed method further include determining a health management status of the patient with respect to a second disease based on the updated patient profile and co-morbidity of the first disease with the second disease. In specific embodiments, the first disease and the second disease are selected from a cardiovascular disease and diabetes.

The recommended action can include, for example, using a beneficial agent such as therapeutics, pharmaceuticals or biologics, using a medical device such as a surgical device, a monitoring device, a corrective device, an implantable device, or an artificial organ, using a nutritional product, using a medical procedure, using a diagnostic test, obtaining related education, altering the patient's diet, modifying the patient's lifestyle, or providing transition services.

In certain embodiments, the recipient of the recommended action can be selected. For example, the recipient can be selected from a patient, a physician, a caregiver, a health care provider, a counselor or a financer. In such embodiments, the recommended action can be based upon the recipient.

In accordance with another aspect of the disclosed subject matter, a system for patient healthcare assessment and management is provided. The system includes at least one memory unit to store a patient profile including patient data and test results, and at least one processing unit operably coupled with the at least one memory unit. The at least one processing unit is operable to screen a patient for a disease based on the patient profile, identify at least one test to assess a state of the disease based on the patient profile, assess the state of the disease based upon results of the at least one test, update the patient profile to include the results of the at least one test and the assessed disease state, determine a health management status of the patient with respect to the disease based on a comparison of the updated patient profile to at least one predefined criterion regarding progression of the disease, and provide a recommended action based on the health management status and the updated patient profile. The system further includes a display operably coupled to the processing unit to display the recommended action for a recipient. Certain embodiments of the system are internet-based, and the recommended action is presented on an internet-enabled display device.

BRIEF DESCRIPTION OF THE DRAWINGS

To provide a more complete understanding of the present invention and the features and advantages thereof, reference is made to the following description taken in conjunction with the accompanying drawings, in which.

DETAILED DESCRIPTION

Figure 1:
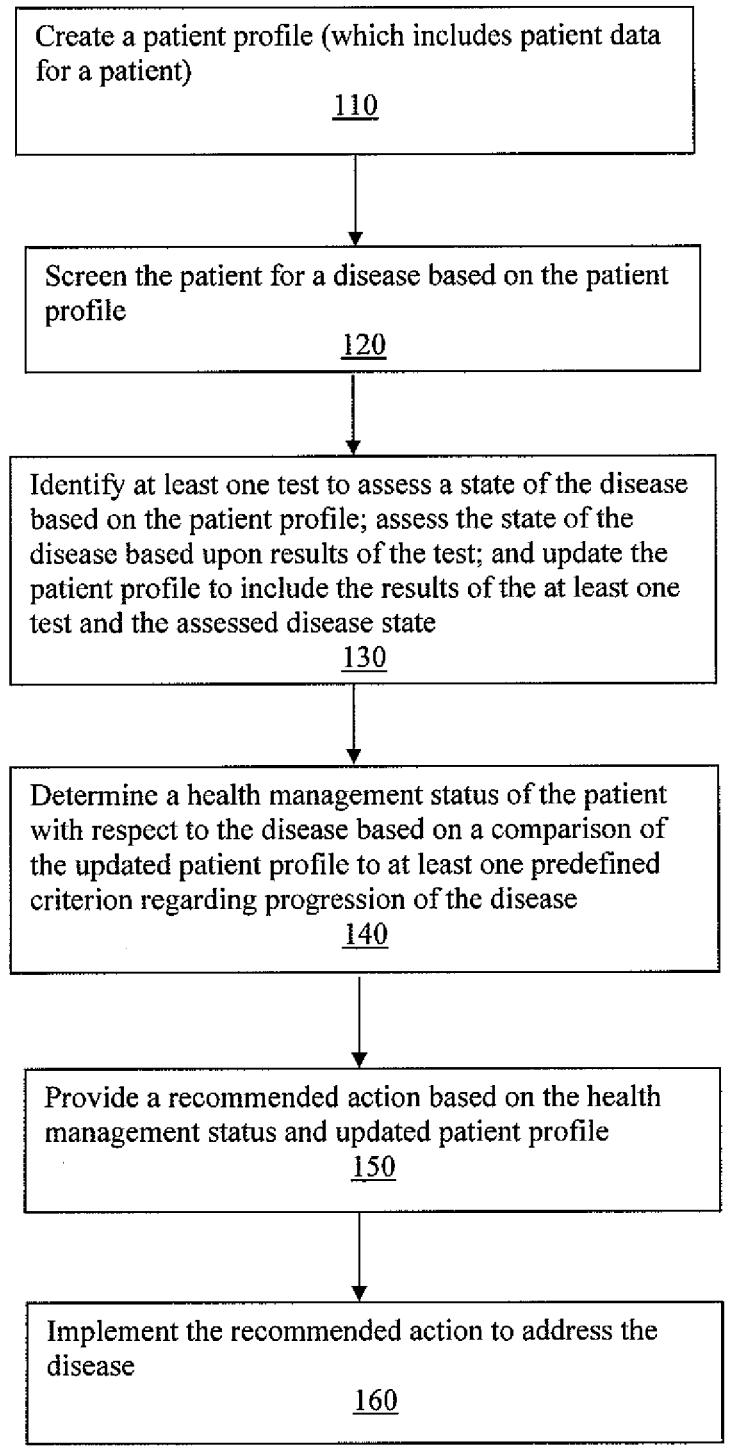
FIG. 1 illustrates a process for the management of healthcare of patients according to some embodiments of the disclosed subject matter.

The disclosed subject matter provides methods and systems for patient healthcare management. The methods and systems include, among others, screening patients for one or more diseases, assessing the patients' health management status with respect to the diseases, and providing treatment options and/or other recommended course of action to address the diseases.

In accordance with the currently disclosed subject matter, a method for patient healthcare management is provided. First, a patient profile is created, which includes patient data for a patient. The patient is then screened for a disease based on the patient profile. Thereafter, at least one test is identified to assess a state of the disease based on the patient profile, and the state of the disease is assessed based upon results of the test. The patient profile is updated accordingly to include the results of the at least one test and the assessed disease state. Based on a comparison of the updated patient profile to at least one predefined criterion regarding progression of the disease, a health management status of the patient with respect to the disease is determined. A recommended action is then provided, and implemented to address the disease.

In accordance with another aspect of the currently disclosed subject matter, a system for patient healthcare management is provided. The system includes at least one memory unit to store a patient profile including patient data and test results, and at least one processing unit operably coupled with the at least one memory unit. The processing unit is operable to support the following operations: screening a patient for a disease based on the patient profile, identifying at least one test to assess a state of the disease based on the patient profile, assessing the state of the disease based upon results of the at least one test, and updating the patient profile to include the results of the at least one test and the assessed disease state, determining a health management status of the patient with respect to the disease based on a comparison of the updated patient profile to at least one predefined criterion regarding progression of the disease, and providing a recommended action based on the health management status and the updated patient profile.

For purpose of illustration and not limitation, reference will be made to a flowchart in FIG. 1, and the exemplary embodiments of FIGS. 2-4, which illustrate certain aspects of the methods for patient healthcare management as applied to diabetes and cardiovascular disease, respectively. Additionally, reference is made to FIG. 5, which illustrates an exemplary embodiment of a system for patient healthcare management. The methods and systems provided herein will be further described in conjunction with each other for understanding and enablement. In some embodiments described below, cardiovascular disease (such as Stroke, Peripheral Arterial Disease, congestive heart failure, and myocardial infarction) and diabetes are used as illustrative target diseases for the disclosed methods and systems; however, similar procedures and systems can be devised for other diseases, including autoimmune diseases (such as rheumatoid arthritis), oncological diseases, pulmonary diseases, neurological diseases, metabolic diseases, infectious diseases, neurodegenerative diseases, chronic lower respiratory disease, pneumonia, and renal diseases.

For purpose of illustration and not limitation, FIG. 1 illustrates an exemplary method for patient healthcare management in accordance with certain embodiments of the disclosed subject matter. At 110, a patient profile is created, which includes patient data for a patient. This can involve obtaining or retrieving patient data from an existing source. As used herein, the patient data includes, without limitation, at least one of the patient's age, weight, gender, ethnicity, diet, lifestyle habits, and pregnancy status. The patient's lifestyle habits include, without limitation, smoking, drinking, exercise, sexual activity, among others as relevant to the particular disease of interest. The patient data can further include the patient's prior medical records or history of medical conditions. In some embodiments, the patient data includes information of the patient's consanguine family members relevant to the disease of interest. The patient data can be obtained from any suitable sources, for example, from filled-out questionnaire by the patient, from the patients' physician's records, a healthcare provider, a healthcare financer, previous claims records of the patient, or any other patient's healthcare related records. In the event that a previous patient profile is available, creating a patient profile includes updating such patient profile to reflect the recent events of the patient, such as lifestyle changes or recent medical history. The patient profile can be stored in a format and manner for easy access and retrieval, e.g., in a computer database, such as the one depicted as 530 in FIG. 5. As illustrative examples, a patient profile can be created for healthcare management with regard to diabetes (at 210 in FIG. 2) and cardiovascular disease (at 310 in FIG. 3), respectively, wherein patient data relevant to these diseases can be respectively obtained and stored.

With reference to FIG. 1 at 120, the patient is screened for a disease based on the patient profile. As used herein, "screen" or "screening" refers to a preliminary assessment of a patient regarding the patient's likelihood of having or risk of developing a disease. The screening (and the later assessment) can be for a preselected disease, e.g., diabetes or cardiovascular disease. Alternatively, the screening (and the later assessment) can be for a disease that the patient is prone to have based on the patient profile, for example and not limitation, based on an evaluation of risk factors in the patient data relevant to the disease, such as the level of physical activity, body weight, and smoking.

Screening a patient can be performed according to a set of criteria established based on the statistical characteristics of the selected disease among populations. The one or more such screening criteria can be selected based on professional clinical practice guidelines in a specialty field for the disease.

Figure 2:
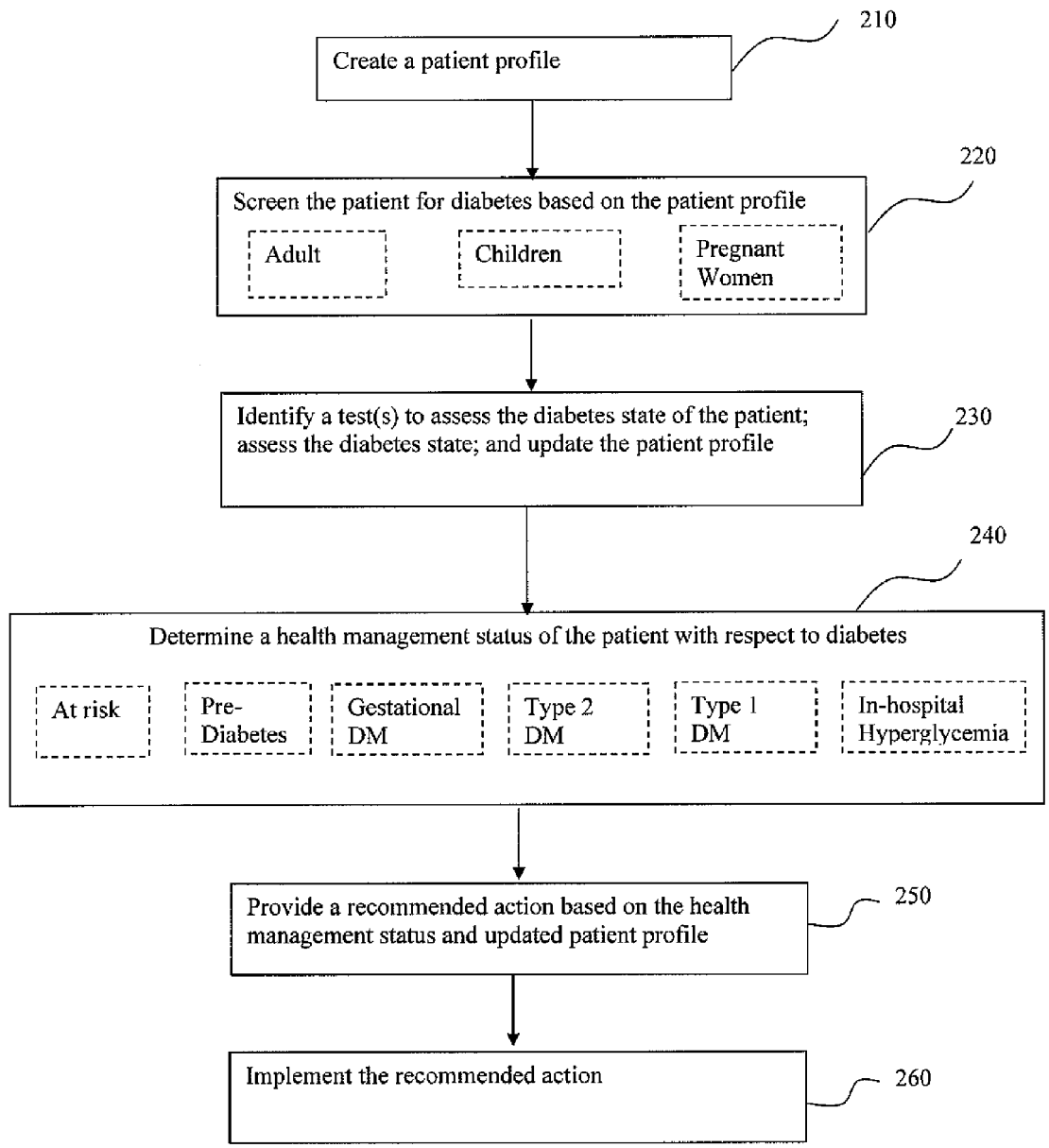
FIG. 2 illustrates an exemplary embodiment of the disclosed subject matter for a process for the management of healthcare of patients, as applied to diabetes.

For purpose of illustration and not limitation, referring to FIG. 2 at 220, in the case of diabetes, different criteria can be established for adults, children, and pregnant women. For nonpregnant adults, further testing (or assessment) can be considered for those who are overweight (BMI>25 kg/m$^2$) and have additional risk factors as follows:

Physical inactivity;
First-degree relative with diabetes;
Members of a high risk ethnic population (e.g., African American, Latino, Native American, Asian American, Pacific Islander);
Women who delivered a baby weighing 9 lb or were diagnosed with GDM;
HCG testing if indicated;
Hypertension (140/90 mmHg or on therapy for hypertension);
HDL cholesterol level 35 mg/dl (0.90 mmol/l) and/or a triglyceride level 250 mg/dl (2.82 mmol/l);
Women with Polycystic Ovarian Syndrome (PCOS);
IGT or IFG on previous testing;
Other clinical conditions associated with insulin resistance (e.g., severe obesity, acanthosis nigricans);
History of cardiovascular disease
Hemoglobin A1C.

For patients who do not meet the above criteria, testing for pre-diabetes and diabetes can begin at age 45. If results are normal, testing can be repeated at least at three year intervals with consideration of more frequent testing depending on initial results and risk status.

For children, further assessment of diabetes can be considered for those children who are overweight (BMI 85th percentile for age and sex, weight or height 85th percentile, or weight 120% of ideal for height) and have any two of the following risk factors:

Signs of insulin resistance;
Family history of type 2 diabetes in first or second degree relative;
Members of a high risk ethnic population (e.g., African American, Latino, Native American, Asian American, Pacific Islander);
Conditions associated with insulin resistance (acanthosis nigricans, hypertension, PCOS, or small for gestational age birth weight)-Other conditions associated with insulin resistance (dyslipidemia);
Maternal history of diabetes or gestational diabetes mellitus (GDM) during the child's gestation.

The screening for diabetes for children can start at age 10 years or at onset of puberty, if puberty occurs at a younger age, and performed, for example every 3 years.

For pregnant women (pregnancy or fertility can be assessed using one or more tests of FLM, FSH, LH, SHBG, Estradiol, Progesterone, Prolactin, Testosterone, and CMV), GDM risk evaluation can be carried out at the first prenatal visit. Women at very high risk for GDM can be further assessed for diabetes as soon as possible after the confirmation of pregnancy, where the criteria for very high risk include Severe obesity;
Prior history of GDM or delivery of large for gestational age infant;
Presence of glycosuria;
Diagnosis of PCOS
Strong family history of type 2 diabetes;

Screening/diagnosis at this stage of pregnancy should use standard diagnostic testing for an adult. Women of greater than low risk of GDM, including those above not found to have diabetes early in pregnancy, can undergo GDM testing at 24-28 weeks of gestation, where low risk status is defined as women with all of the following characteristics:

Age<25 years;
Weight normal before pregnancy;
Member of an ethnic group with a low prevalence of diabetes;
No known diabetes in first degree relatives;
No history of abnormal glucose tolerance;
No history of poor obstetrical outcome.

In certain embodiments, the screening include one or more screening tests based on the patient data to increase the reliability of the screening. For example, after considering the body weight and risk factors, a screening test for fasting plasma glucose (FPG) can be performed. Oral glucose tolerance test (OGTT) or Hemoglobin A1C test can also be performed. The patient profile can be updated to include the results of the screening test.

In certain embodiments, the screening for a patient is performed periodically, e.g., yearly or bi-yearly, and such screening can include different check items at different time intervals. For example, in the case of cardiovascular disease (FIG. 3 at 320), the following items can be checked for at least each year:

Current and past use of alcohol, illicit drugs, alternative therapies, chemotherapy drugs and tobaccos;
Diet and family history of heart disease;
Ability to perform activities of daily living ("ADL");
Exercise monitoring;
Weight;
Blood pressure screening.

For at least every two years, the following items can be checked:

Orthostatic blood pressure;
Body mass index;
Waist circumferences;
Pulse; and
Blood pressure screening.

For every two to five years depending on risk, the following items can be checked:

Fasting serum lipoprotein;
Fasting blood glucose;

Risk assessment (Farmingham risk score); and
Hemoglobin A1C.

Screening for cardiovascular disease or other diseases may be not available for certain patients due to their acute medical conditions or hospitalization. These patients can be included in the assessment for the selected disease as described in the procedures below.

As used herein, the professional guidelines for identifying appropriate screening criteria (or screening test) for certain embodiments include those clinical practice guidelines published by a professional organization in the specialty field relating to the selective disease, official statements regarding clinical practice issued by a relevant government body. For example, for diabetes, relevant guidelines can include guidelines published by American Diabetes Association; for cardiovascular disease, relevant guidelines include guidelines published by American Heart Association (AHA), American College of Cardiology (ACC), and American Stroke Association (ASA). These guidelines may be updated from time to time to incorporate new developments in the specialty field. Exemplary guidelines for diabetes include:

(1) American Diabetes Association. (2009) "Standards of Medical Care in Diabetes—2009." Diabetes Care, Volume 32, Supplement 1, January 2009: S13-S61.
(2) American Diabetes Association. (2009). "Living With Diabetes." Treatment & Care, 2009, available at http://www.diabetes.org/living-with-diabetes/treatment-and-care/.
(3) Department of Health (UK). "Five years on—Delivering the Diabetes National Service Framework." August 2008, 1-44.

Exemplary guidelines for cardiovascular disease include:

(1) American Heart Association. "2009 Focused Update Incorporated Into the ACC/AHA 2005 Guidelines for the Diagnosis and Management of Heart Failure in Adults: A Report of the American College of Cardiology Foundation/American Heart Association Task Force on Practice Guidelines: Developed in Collaboration with the International Society for Heart and Lung Transplantation." Circulation (2009): e391-479.
(2) American Heart Association. "AHA Guidelines for Primary Prevention of Cardiovascular Disease and Stroke: 2002 Update: Consensus Panel Guide to Comprehensive Risk Reduction for Adult Patients Without Coronary or Other Atherosclerotic Vascular Disease." Circulation (2002): 388-391.
(3) American Heart Association. "Guidelines for the Early Management of Adults With Ischemic Stroke: A Guideline From the American Heart Association/American Stroke Association Stroke Council, and the Atherosclerotic Peripheral Vascular Disease and Quality of Care Outcomes in Research Interdisciplinary Working Groups: The American Academy of Neurology affirms the value of this guideline as an educational tool for neurologists." Circulation (2007): e478-e534.
(4) American Heart Association. "AHA/ACC Guidelines for Secondary Prevention for Patients With Coronary and Other Atherosclerotic Vascular Disease: 2006 Update: Endorsed by the National Heart, Lung, and Blood Institute." Circulation (2006): 2363-2372.
(5) Michael S. Lauer. "Primary Prevention of Atherosclerotic Cardiovascular Disease: The High Public Burden of Low Individual Risk." Journal Of the American Medical Association (2007): 1376-1378.
(6) American Heart Association. "American Heart Association Guidelines for Primary Prevention of Atherosclerotic Cardiovascular Disease Beginning in Childhood." Circulation (2003): 1562-1566.
(7) American Heart Association. "ACC/AHA 2005 Guidelines for the Management of Patients With Peripheral Arterial Disease (Lower Extremity, Renal, Mesenteric, and Abdominal Aortic)." Journal of the American College of Cardiology (2006): 1239-1312.
(8) American Society of Nephrology "Microalbuminuria as an Early Marker for Cardiovascular Disease" Journal of American Society of Nephrology 17 (2006): 2100-2105.
(9) United States Preventive Services Task Force Clinical Preventive Services Pocket Guide 2009, pg 3-10.

The above guidelines are hereby incorporated by reference in their entireties.

With reference to FIG. 1 at 130, at least one test is identified to assess a state of the disease based on the patient profile, and the state of the disease is assessed based upon results of the test. Then, the patient profile is updated to include the results of the at least one test and the assessed disease state. The test can include the examination of the patient's past medical record. In certain embodiments, the at least one test for assessing the state of the disease includes at least one diagnostic test, which can be a lab test or physical examination. The diagnostic test can be selected according to professional guidelines relating to the disease, as those noted above for patient screening.

Using diabetes for illustration, the screening of the patient can suggest that the patient is likely to be either at risk for diabetes, or likely to have developed a condition of diabetes. If the patient is determined to be at risk for diabetes in the screening, further tests can be used to assess or confirm this preliminary determination (FIG. 2 at 230). For example, the tests can include lab tests on the below items:

Medical history, including age and characteristics of onset of diabetes (e.g., DKA, asymptomatic laboratory finding); eating patterns, physical activity habits, nutritional status, and weight history; growth and development in children and adolescents;

Physical examination including height, weight, BMI; blood pressure determination, including orthostatic measurements when indicated; and fundoscopic examination;

Lab tests including fasting blood glucose; lipid profile; liver function tests; and serum creatinine On the other hand, if the patient is determined in the screening to have developed a condition of diabetes, further diagnostic tests, including lab tests, physical exam, and other diagnosis using medical equipment or devices can be performed to further assess the state of diabetes (FIG. 2 at 230). For example, for preliminary diagnosis of Pre-Diabetes, lab tests can be performed (e.g., using the following criteria: Impaired fasting glucose=100 mg/dl to 125 mg/dl; Impaired glucose tolerance=2-h plasma glucose 140 mg/dl to 199 mg/dl); for preliminary diagnosis of Gestational Diabetes Mellitus, lab tests can be performed (e.g., using the following criteria: at least two of the following plasma glucose values must be found: Fasting: ≥95 mg/dl; 1 h: ≥180 mg/dl; 2 h: ≥155 mg/dl; 3 h: ≥140 mg/dl); for preliminary diagnosis of Diabetes Mellitus, lab tests can be performed (e.g., using one of the following criteria: (a) FPG 126 mg/dl (7.0 mmol/l); (b) Symptoms of hyperglycemia (including e.g., polyuria, polydipsia, and unexplained weight loss) and a casual plasma glucose 200 mg/dl (11.1 mmol/l); or (c) 2-h plasma glucose 200 mg/dl (11.1 mmol/l) during an OGTT.)

In addition to these diagnoses for different types of diabetes based on lab tests, further examination of patient data including the patient's medical history, physical exam, and lab evaluation can be included in the assessment of the state of diabetes. The examination of medical history can include, without limitation:

Age and characteristics of onset of diabetes (e.g., DKA, asymptomatic laboratory finding);
Eating patterns, physical activity habits, nutritional status, and weight history; growth and development in children and adolescents;
Diabetes education history;
Review of previous treatment regimens and response to therapy (A1 C records);
Current treatment of diabetes, including medications, meal plan, physical activity patterns, and results of glucose monitoring and patient's use of data;
DKA frequency, severity, and cause;
Hypoglycemic episodes;
Hypoglycemia awareness;
Any severe hypoglycemia: frequency and cause;
History of diabetes-related complications;
Microvascular: retinopathy, nephropathy, neuropathy (sensory, including history of foot lesions; autonomic, including sexual dysfunction and gastroparesis);
Macrovascular: CHD, cerebrovascular disease, PAD;
Other: psychosocial problems, dental disease.

Physical examinations can include, without limitation:
Height, weight, BMI;
Blood pressure determination, including orthostatic measurements when indicated;
Fundoscopic examination;
Thyroid palpation;
Skin examination (for acanthosis nigricans and insulin injection sites);
Comprehensive foot examination;
Palpation of dorsalis pedis and posterior tibial pulses;
Presence/absence of patellar and Achilles reflexes;
Determination of proprioception, vibration, and monofilament sensation. Lab evaluation can include, without limitation:
A1C, if results not available within past 2-3 months (if not performed/available within past year;
Fasting lipid profile, including total, LDL- and HDL-cholesterol and triglycerides;
Liver function tests;
Test for urine albumin excretion with spot urine albumin/creatinine ratio;
Serum creatinine and calculated GFR;
Thyroid-stimulating hormone in type 1 diabetes, dyslipidemia or women over age 50.

Using cardiovascular disease for illustration, the screening of the patient can suggest that the patient is likely to be either at risk for cardiovascular disease, or likely to have developed a condition of cardiovascular disease (such as vascular disease and coronary artery disease). If the patient is determined to be at risk for cardiovascular disease in the screening, further tests can be used to assess or confirm this preliminary determination (FIG. 3 at 330). For example, the tests can include lab tests on the below items:
Complete blood count;
Urinalysis;
Serum electrolytes;
Blood urea nitrogen;
Serum creatinine;
Fasting blood glucose;
Lipid profile;
Liver function tests;
Thyroid-stimulating hormone;
Hemoglobin A1C for if the patient is diabetic;

In addition, the following diagnostic tests can be performed for the assessment:
Chest x-ray;
Two-dimensional echocardiography with Doppler;
Twelve-lead electrocardiogram;
HIV.

If the patient is determined in the screening to likely have developed a condition of cardiovascular disease (FIG. 3 at 330), further diagnostic tests, including lab tests, physical exam, and other diagnosis using medical equipment or devices such as MRI and cardiograph can be performed to further assess the state of the cardiovascular disease. For example, if the patient is determined to have likely developed a vascular condition (such as Stroke, Albuminuria, Peripheral Arterial Disease (PAD), Erectile Dysfunction), the following tests can be used for the assessment:
Complete blood count, including platelet count;
Fasting blood glucose;
Serum creatinine/renal function tests;
Hemoglobin A1C if the patient is diabetic;
Prothrombin time;
Neurological evaluation;
Renal function;
Lipid profile;

In addition, the following diagnostic tests can be performed for the assessment:
Computed tomography ("CT") imaging;
MRI;
Electrocardiogram;
Markers of cardiac ischemia;
Cardiac monitoring, including Cardiac enzyme tests;
Doppler ultrasonography;
Carotid duplex sonography;
Catheter angiography;
Contrast angiography;
Treadmill exercise testing;
MRA.

If the patient is determined to have likely developed a coronary artery disease (such as angina, congestive heart failure, or myocardial infarction), the following lab/diagnostic tests can be used for the assessment:
Hemoglobin A1C if the patient is diabetic;
Urinalysis;
Serum electrolytes;
Blood urea nitrogen;
Serum creatinine;
Fasting blood glucose;
Lipid profile;
Liver function tests;
Thyroid-stimulating hormone;
Measurement of natriuretic peptides (BNP);
NT-proBNP;
Twelve-lead electrocardiogram;
Chest radiograph;
Two-dimensional echocardiography with Doppler;
Radionuclide ventriculography
Coronary arteriography;
Maximal exercise testing (with or without measurement of respiratory gas exchange);
Holter monitoring;
Measurement of ejection fraction ("EF");
Computed tomography;
MRI.

The patient who is determined to have likely developed one of the conditions in cardiovascular disease can be further screened and assessed for other conditions, for example, hemochromatosism, sleep disturbed breathing, rheumatologic diseases, amyloidosis, or pheochromocytoma.

Based on the results of the one or more tests for assessing the disease at issue, the state of the disease can be determined, and the patient profile updated to include the results of the tests and the assessed disease state. The assessed state can include a set of elements, each representing a characterization of results of different tests used in the assessment. Such characterization can be a conditional statement whether a tested item, such family history of heart disease, exists, or alternatively, whether the measured value, such as serum creatinine level, of a tested item meets or exceeds a predetermined threshold value.

With reference to FIG. 1 at 140, a health management status of the patient with respect to the disease is determined based on a comparison of the updated patient profile to at least one predefined criterion regarding progression of the disease that requires different level or options of care. The at least one predefined criterion can be obtained from the expert knowledge in the specialty field, for example, from the above-noted guidelines for diabetes and cardiovascular disease. The comparison of the updated patient profile to at least one predefined criterion regarding progression of the disease can be based on an indicator or index computed based on an evaluation of weighted factors assigned to the multiple elements of assessed diseases state as well as other information in the patient profile relevant to the disease.

For purpose of illustration and not limitation, for diabetes, a patient's health management status can include the following stages of diabetes: at risk for diabetes, pre-diabetes (i.e., at high risk for diabetes with impaired fasting glucose or impaired glucose tolerance), and different types of diabetes (e.g., gestational DM, type 1 DM, type 2 DM) (FIG. 2 at 240). For cardiovascular disease, based on the updated patient profile, a patient's health management status can include following stages of cardiovascular disease: at risk, affected, sick, and surviving (FIG. 3 at 340).

In addition, the healthcare status of the patient with respect to the disease at issue can further include one or more additional indicators characteristic of a patient population corresponding to the patient. For example, for a patient at risk of diabetes, the indicators can include: hypertension, high risk ethnic population, family history of Diabetes mellitus, atherosclerotic disease, and physical inactivity. For a pre-diabetes patient, the indicators can include: impaired fasting glucose; impaired glucose tolerance; severe obesity; abnormal cholesterol level; and abnormal triglyceride level. For a gestational DM patient, the indicator can include: prior history of GDM or delivery of large for gestational age infant; presence of glycosuria; women with Polycystic Ovarian Syndrome; and strong family history of type II diabetes. For a type 2 DM patient, the indicators can include obesity, insulin resistance, dyslipidemia, family history of type 2 DM or maternal history of DM; acanthosis nigricans; polycystic varian syndrome (PCOS), high risk ethnic population, hypertension, Diabetic Ketoacidosis (DKA). For a type 1 DM patient, the indicators can include elevated blood glucose level, hyperglycemia, family history of type 1 DM, and DKA. For a patient who is hospitalized with hyperglycemia with a medical history of diabetes, the indicators can include unrecognized diabetes occurring during hospitalization and confirmed as diabetes, hospital related hyperglycemia, and DKA.

For cardiovascular disease, a patient at risk can have indicators that include the following: hypertension; atherosclerotic disease; diabetes mellitus, pre-DM, obesity, metabolic syndrome, hyperlipidemia, using cardiotoxins, family history of cardiomyopathy, albuminuria, and hormone therapy. An affected cardiovascular disease patient may have an indicator including the following: myocardial infarction ("MI"); left ventricular ("LV") remodeling; low ejection fraction ("EF"); asymptomatic valvular disease; cardiomyopathyl and arrhythmia. Another set of indicators for affected patient can include Peripheral Artery Disease, claudication, hyperproteinuria, erectile dysfunction; disorders of aorta, mesenteric, renal and lower extremity arteries. A patient sick with cardiovascular disease can have indicators that include structural heart disease, shortness of breath, fatigue, congestive heart failure, and reduced exercise tolerance. A patient surviving with cardiovascular disease can have indicators that include chronic hypertension, hypotension, both fluid overload and shock, marked symptoms despite maximal medical therapy, volume overload, shock syndrome, renal insufficiency, cardiomyopathy, cardiac cachexia, and congestive heart failure.

With reference to FIG. 1 at 150, a recommended action is provided, based on the health management status and updated patient profile, to address the disease, including primary prevention of the onset of the disease (or wellness management), further diagnosing or treating the disease, and preventing the further progression of the disease. For example, for diabetes patients, a recommended action can be provided depending on whether a patient is at risk, determined to have pre-diabetes, or have various types of diabetes (FIG. 2 at 250). For cardiovascular patients, a recommended action can be provided depending on whether a patient is at risk, affected, sick, or surviving with a cardiovascular disease (FIG. 3 at 350). The professional guidelines as above discussed (e.g., those published by ACC, AHA, and ADA) can be utilized in making the recommended action. The recommended action can be provided to a recipient on an internet-based system, and can be visually displayed or otherwise presented on a display device.

For example, the recommended action can include, without limitation, using a beneficial agent such as therapeutics, pharmaceuticals or biologics, using a medical device such as a surgical device, a monitoring device, a corrective device, an implantable device, or an artificial organ, using a nutritional product, using a medical procedure, using a diagnostic test, obtaining related education, altering the patient's diet or modifying the patient's lifestyle, and scheduling or reminders for any of the above courses of action. In some embodiments, the recommended action can also include identifying where the patient can seek related products, treatment, procedures, tests, education or counseling.

In certain embodiments, the recommended action includes providing transition services to the patient. The transition services can include education, training, adherence, reimbursement assistance, counseling, and transportation for a patient, and can further include services that allow a patient to be transitioned from in-patient care setting to ambulatory, home or other settings, such as home health monitoring.

In certain embodiments, the recommended action includes the patient's forbearance from engaging in certain activities that may have adverse effects on the disease at issue. For example, a recommended action can be avoidance of smoking, alcohol consumption, and other habits of a patient, or the use of certain drugs that may adversely impact the disease condition or interfere with the treatment option for the disease.

The recommended action can be provided to a variety of different recipients, for example, to a patient, a physician, a caregiver, a health care provider, a counselor or a financer. Accordingly, the recommended action can be provided to a recipient in an internet-enabled display in a variety of settings of care, as required or desired by the recipient. These settings of care can include, but are not limited to, clinics, pharmacies, hospitals, physicians' offices, patients' homes, or other locations such as an office of an insurer, a medical product provider, or other healthcare stakeholders or participants. In addition, the currently disclosed subject matter includes selecting whether the recommended action to a recipient such as those noted above. The recommended action can be tailored to or based upon the recipient. For example, if a recommended action is to be provided to a patient, the recommended action can include instructions for the patient where to seek care, suggestions that the patient should refrain from taking certain food or drugs, or a list for the patient treatment options and associated cost. If a recommended action is to be provided to a healthcare provider, the recommended action can include recommendations regarding prescription, medical devices, or medical procedures that can be used for treating the disease or preventing the further progression of the disease. The recommended action can be further based upon any specific requirements provided by a recipient, such as the budget constraint from a patient or a financer, or reimbursement cost criteria for a financer. Further, the recommended action can be based upon a plurality of considerations including treatment options with the associated cost, and prognosis of such treatment options, such that a cost-effective and optimized treatment option may be selected and that informed decision can be made by the patient or other involved healthcare participants.

The recommended action can include actions designed to meeting a set of goals appropriate for the determined health management status. Using diabetes as an example, and with reference to FIG. 2 at 250, different sets of goals can be set for patients having different health management statuses. For a patient at risk of diabetes, the goals can include: annual checkup with a healthcare provider; prevention and delay of DM through early detection and treatment of risk factors; medical nutrition therapy (including increasing fiber intake); diagnosis and treatment of cardiovascular disease; lifestyle counseling; increase in physical activity (>150 minutes per week of moderate activity); weight management (weight loss of 5-10% of body weight); lifestyle counseling; and smoking cessation.

For a patient with a health management status of pre-diabetes, the goals can include prevention/delay of DM through early detection and treatment of risk factors; increase physical activity (>150 minutes per week of moderate activity); annual checkup with a healthcare provider; diagnosis and treatment of cardiovascular disease; medical nutrition therapy (including increasing fiber intake); hypertension and blood pressure control; dyslipidemia/lipid screening and management; retinopathy screening and treatment; neuropathy screening and treatment; weight management (weight loss of 5-10% of body weight); lifestyle counseling; smoking cessation; and nephropathy screening and treatment.

For a patient with a health management status of gestational DM, the goals can include glycemic control; medical nutrition therapy; prevention of post partum diabetes; screening 6-12 weeks post partum; and SMBG (3 or more times daily). Recommended medical intervention can include routine use of Human Insulin therapy, and SMBG (3 or more times daily). The patient should be recommended against oral hypoglycemic medications and glyburide.

For a patient with a health management status of Type 2 DM, the goals can include all the goals under pre-diabetes, and additionally: diabetes self-management education; glycemic control; A1C<7.0%; medical nutrition therapy; management of underlying cardiovascular disease; psychosocial assessment and care; celiac disease management; hypothyroidism management; decrease to moderate levels of alcohol consumption; and foot care. Recommended drugs/interventions include metformin in combination with lifestyle changes; oral hypoglycemic medications; insulin therapy; and bariatric surgery. The patient should be recommended against routine supplementation with antioxidants (e.g. Vitamins E and C, and carotene).

For a patient with a health management status of Type 1 DM, the goals can include those under DM Type 2, and additionally: matching of prandial insulin to carbohydrate intake, premeal blood glucose, and anticipated activity; diabetes self-management education (including appropriate use and interpretation of SMBG data); self monitoring of blood glucose (SMBG); A1C (point of care testing at least twice a year with quarterly tests in those patients who have had changes in therapy)—adolescents and children: >7.5% but <8.5% for Ages 0-6, <8% for Ages 6-12<7.5% for ages 13-19. Recommended drugs/interventions can include the use of multiple dose insulin injection (e.g., 3-4 injections per day of basal and prandial insulin or continuous subcutaneous insulin infusion) therapy; insulin pump therapy; SMBG (3 or more times daily); continuous glucose monitoring may be an option; use of insulin analogs—especially if hypoglycemia is a problem. The patient should be recommended against routine supplementation with antioxidants (e.g. Vitamins E and C, and carotene).

For a hospitalized patient with hyperglycemia, the goals can include same glycemic goals as patients with known diabetes, and additionally: glucose monitoring for patients with high risk for hyperglycemia, high dose of glycocorticoids therapy; self monitoring of blood glucose for selected patients; enteral or parenteral nutrition, intravenous insulin protocol for critically ill patients; basal/bolus therapy for selected patients; A1C if the result of testing in the previous 2-3 months is not available/Estimated Average glucose (eAG); and "Survival skills education" and follow up for each patient. Recommended drug interventions can include the use of insulin injection therapy and medication such as octreotide or immunosuppressive. The patient should be recommended against sliding-scale insulin regimens as mono-therapy.

Figure 3:
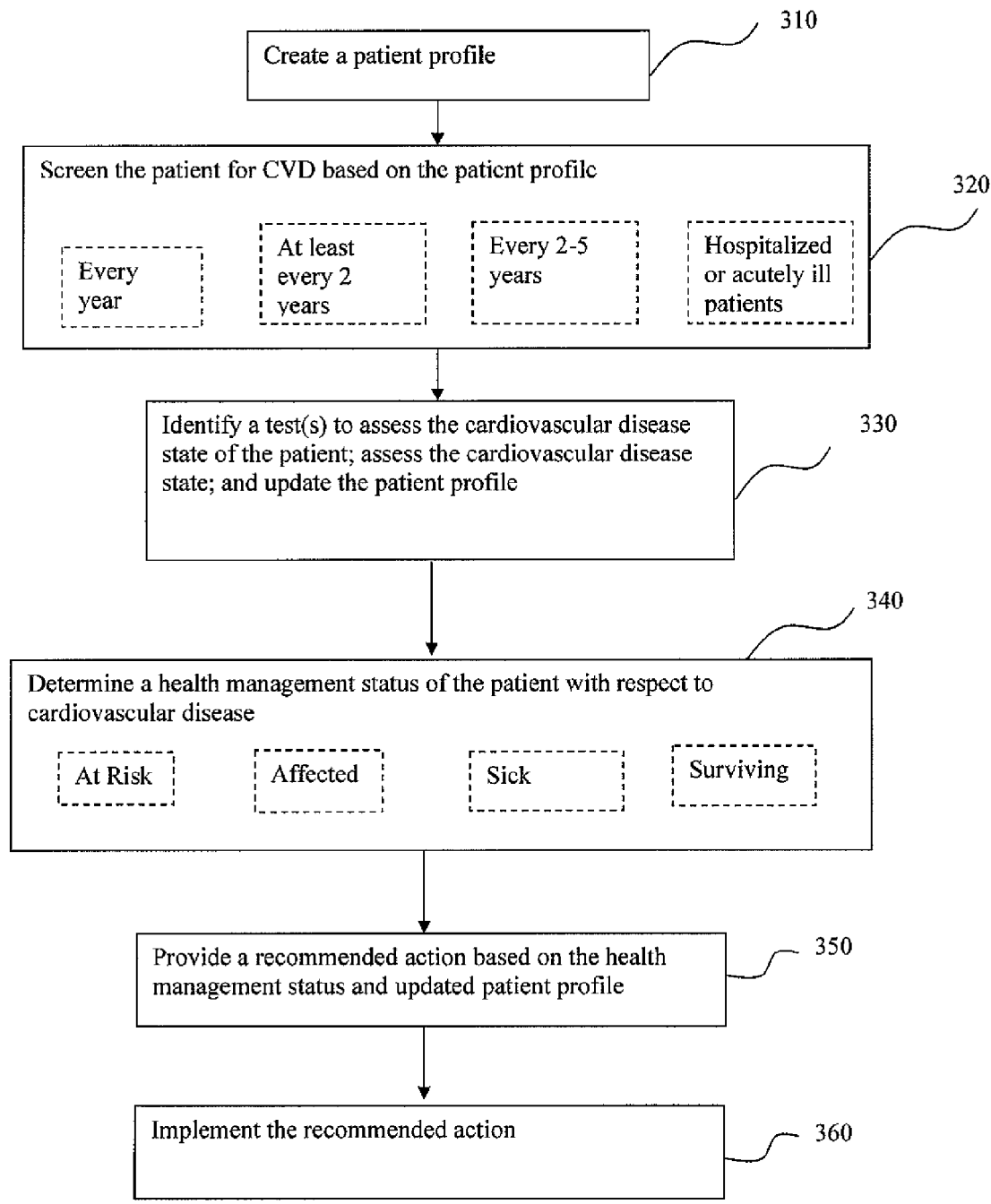
FIG. 3 illustrates an exemplary embodiment of the disclosed subject matter for a process for the management of healthcare of patients, as applied to cardiovascular disease.

Using cardiovascular disease as another example, and with reference to FIG. 3 at 350, different sets of goals can be set for patients having different health management statuses. For prevention of, or a patient at risk of cardiovascular disease, the set of goals can include: regular exercise, weight management, monitoring dietary intake, control of systolic and diastolic hypertension, smoking cessation, control alcohol intake and illicit drug use, blood lipid management (HDL, LDL, triglycerides), control of metabolic syndrome, blood sugar level control for patients with diabetes mellitus, diabetes management; ventricular rate or sinus rhythm management, and thyroid disorder treatment. Recommended drugs for the at risk patient with cardiovascular disease can include anti-platelet agents/anticoagulants, aspirin, smoking cessation drugs, and levothyroxine. A patient at risk of cardiovascular disease can be recommended against routine use of nutritional products.

For a patient affected by cardiovascular disease and having indicators including myocardial infarction, LV remodeling, low EF, asymptomatic valvular disease, cardiomyopathy, and arrhythmia, the set of goals can include all previous appropriate measures, treatment after an acute MI, improved arterial flow through coronary revascularization, valve replacement or repair, and secondary prevention of atherosclerotic vascular disease. The recommended drugs for a patient having this health management status can include ACEI or ARB;

beta blockers; antiarrhythmic, antithrombotic, antiplatelet, aldosterone antagonist; and statins. The recommended device can be implantable defibrillators. The patient should be recommended against using digoxin, calcium channel blockers, or nutritional products.

For a patient affected by cardiovascular disease and having indicators including Peripheral Artery Disease, claudication, hyperproteinuria, erectile dysfunction; disorders of aorta, mesenteric, renal and lower extremity arteries, the set of goals can include: rapid identification and evaluation of stroke, use of stroke chain of survival, secondary prevention; assess risk factors for CV disease, history of drug abuse, migraine, seizure, trauma, infection or pregnancy; identification of concurrent MI, vascular conditions, hepatic dysfunction coagulopathies or platelet disorders; assessment for PAD for walking impairment, claudication, ischemic rest pain, family history of first order relative with AAA; comprehensive risk factor modification and antiplatelet therapy; CV assessment if the patient has critical limb ischemia; evaluation to define anatomic level of occlusion and prompt endovascular or surgical revascularization; and nephropathy screening and treatment. Recommended drugs can include oxygen, antiarrhymics, antithrombotics aspirin; enteral, parenteral feedings, ACE, antihypertensives, statins, fibric acid derivatives, ARB, folic acid, and B12. The patient should be counseled against complex imaging studies if he or she has claudication, bypasses to tibial arteries with prosthetic material, and using nutritional products.

For a patient having a health management status of being sick with cardiovascular disease, the goals for recommended course of action can include all previous appropriate measures (i.e., for at risk and affected stages of cardiovascular disease), and additionally, maximal exercise monitoring & evaluation, dietary salt restriction, and cardiac resynchronization therapy. Drugs that can be recommended include duretics for fluid retention, angiotensin-converting enzyme inhibitor, and beta blockers, whereas in selected patients the drugs can further include aldosterone, antagonist, angiotensin II receptor blocker ("ARB"), digitals, and hydralazine/nitrates. Recommended devices in selected patients include biventricular pacing, and implantable defibrillators.

For a patient having a health management status of surviving with cardiovascular disease, the goals for recommended course of action can include all previous appropriate measures as well as oxygen therapy and invasive hemodynamic monitoring. The recommended drugs can include intravenous loop diuretics, intravenous inotropic or vasopressor drugs, angiotensin-converting enzyme inhibitor ("ACEI") or Angiotensin II receptor blocker ("ARB") and beta blockers, cardiac catheterization and revascularization, vasodilators, and extraordinary measures such as heart transplant, chronic inotropes, permanent mechanical support, experimental surgery or support.

In certain embodiments, the method for management of patient care of the disclosed subject matter further includes determining the health management status of the patient with respect to a second disease (e.g., one or more other diseases) based on the updated patient profile and co-morbidity of the first disease with the second disease. In certain embodiments, based on the co-morbidity data on cardiovascular disease and diabetes, the patient's state with respect to diabetes can be assessed at various points in the screening and/or assessment of cardiovascular disease for the patient, and vice versa. For example, if in the assessment of a patient for diabetes, the results for lab tests for the patient's lipid profile indicate that the patient is likely affected by cardiovascular disease, the procedures for screening and/or assessment for cardiovascular disease as described above can be performed for the patient. As another example, if a patient have been assessed as having a Type 2 DM, he or she can be further screened and/or assessed for cardiovascular disease using the screening/assessment procedures described above for cardiovascular disease. Accordingly, recommended actions can be provided based on the health management statuses of the patient with respect to both diabetes and cardiovascular disease.

Other co-morbidity correlation between different diseases or states of different diseases that are known in the field can be similarly used for screening and/or assessing diseases other than the disease targeted in the initial screening. For example, as noted above, in the screening/assessment of vascular or coronary artery disease, rheumatologic diseases can be screened and/or assessed using similar procedures as outlined for diabetes and cardiovascular disease. As another example, the assessment and recommend action for a pre-diabetes patient can include nephropathy (or generally, kidney disease) screening and treatment.

Figure 4:
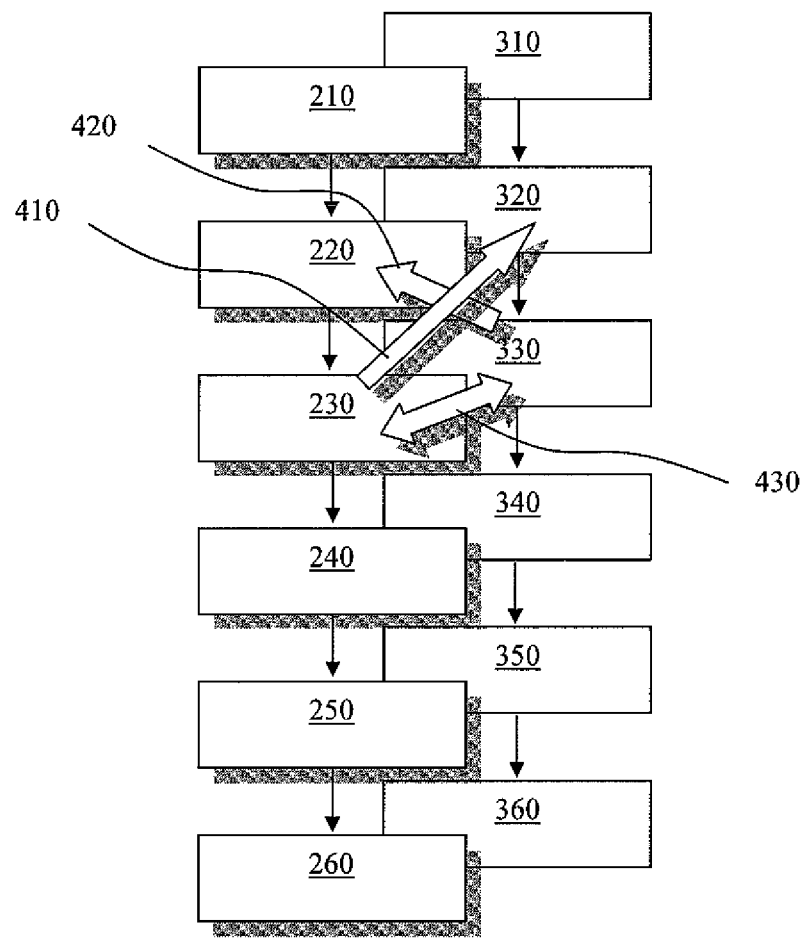
FIG. 4 illustrates an exemplary embodiment of the disclosed subject matter for a process for the management of healthcare of patients.

FIG. 4 illustrates a process of healthcare management process utilizing an exemplary co-morbidity correlation between diabetes and cardiovascular disease as discussed above. Shown on the left (210 through 260) is a previously described process for healthcare management of the disclosed subject matter as applied to diabetes, where the same reference numerals are used to represent the same process steps in FIG. 2. Shown on the right (310 through 360) is a previously described process for healthcare management of the disclosed subject matter as applied to cardiovascular disease, where the same reference numerals are used to represent the same process steps in FIG. 3. Arrows 410, 420, and 430 represent co-morbidity links between the different stages of the healthcare management method of the disclosed subject matter as applied to diabetes and cardiovascular disease, as noted above. Other co-morbidity links can exist between other stages of diabetes and cardiovascular disease, for example, between 240 and 340, between 230 and 340, and between 240 and 330. These co-morbidity links introduce another dimension to the "linear" health management process previously described, that is, the healthcare management process for one disease can change course at various junctures along its normal linear path to proceed on the healthcare management process for another disease. In this manner, the healthcare management method of the disclosed subject matter provides an integrated approach to address interrelated diseases for an overall better outcome for the patient care.

With reference to FIG. 1 at 160, the recommended action is implemented to address the disease. Implementation of a recommended question includes carrying out the recommended action by the recipient of the recommended action. For example, if a recommendation to use a certain drug is provided to a patient, the patient can take the drug as prescribed, thereby implementing the recommendation. If a recommendation is provided to a physician for further testing the patient for a second disease or condition, the physician can perform such test to implement the recommendation. For illustration and not limitation, with reference to FIG. 2 at 260 and FIG. 3 at 360, a recommended action is implemented as appropriate to address the respective diabetes and cardiovascular disease.

Figure 5:
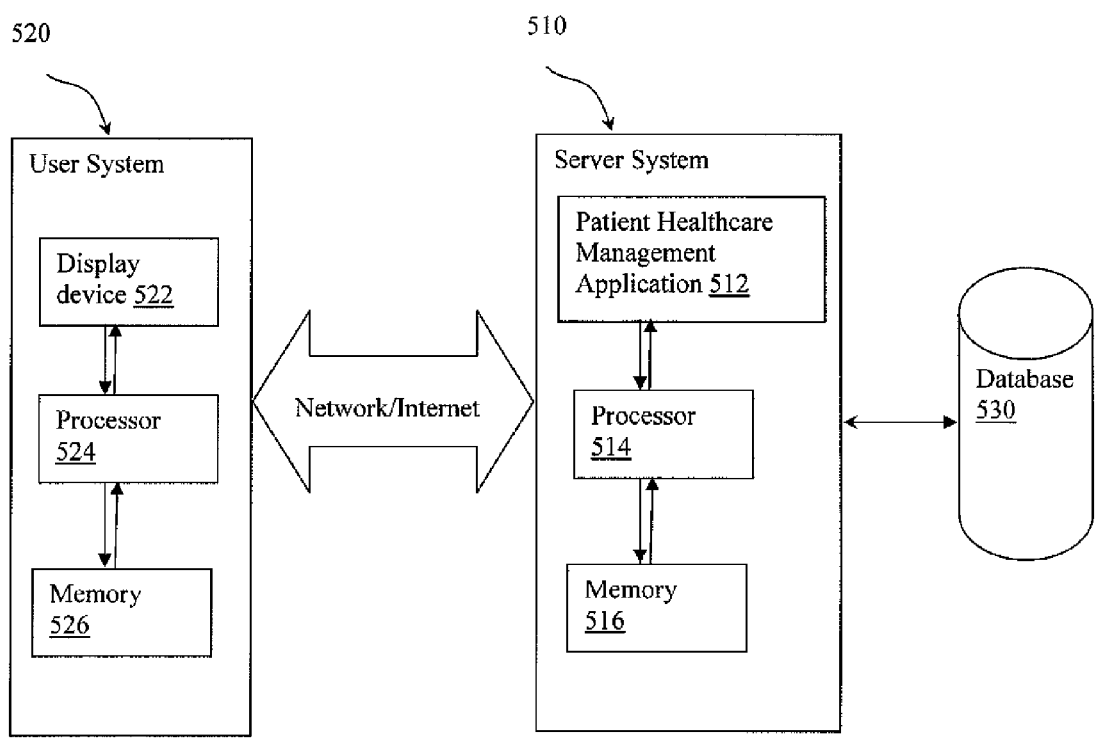
FIG. 5 illustrates a system for the management of healthcare of patients according to some embodiments of the disclosed subject matter.

As previously noted, FIG. 5 illustrates an exemplary embodiment of the healthcare management system of the disclosed subject matter for performing the operations of the method as described above. Collectively, these operations can be implemented in a computer program, herein referred to as the "patient healthcare management application." The program can be implemented as a software component of a suitable hardware platform, for example, a standalone computer, a networked computer, a network server computer, or the like, using appropriate software development tools available for the respective hardware platforms. The healthcare management system also includes a display operably coupled to the processing unit to display the recommended action for a recipient. The system can be implemented in a client-server or distributed systems. For example, the system can be internet-based, and the recommended action can be presented on an internet-enabled display device, e.g., a web browser on a personal computer, PDA, smart phone, or other devices. The patient data for the patient profile can be retrieved from a database externally linked to the system, for example, through a common database connectivity tool, or any other suitable database access protocol.

With reference to FIG. 5, the embodied patient health management system includes a server system 510 which includes the patient healthcare management application 512, and one or more electronic computing devices operable to receive, transmit, process, and store data associated with healthcare management application 512. For example, server system 510 may include one or more general-purpose personal computers, work stations, supercomputers, and include a processor 514 and a memory 516. The patient profile can be stored in the memory 516, and can be retrieved from, and updated into, an external or internal database 530. Although server system 510 is referred to as a "server," the present invention contemplates server system 510 comprising any suitable type of processing device or devices. Database 530, although primarily described as being a "database," may include any suitable memory module and may take the form of volatile or non-volatile memory, including, without limitation, magnetic media, optical media, RAM, ROM, removable media, or any other suitable local or remote memory component. Any suitable number of databases 530 may be used in conjunction with the server system 510.

The embodied patient health management system also includes at least one user system 520 which includes a display device 522 for displaying or otherwise (via audio, audiovisual, visual, or other medium) presenting to a user the recommended action provided by the patient healthcare management application, and a processor 524 and a memory 526 (and network interface(s)) for transmitting, formatting, manipulating information received from the server via a network or internet into a suitable format capable of being presented by the device 522. The user system may also include any appropriate input devices (such as a keypad, touch screen, mouse, or other device that can accept information), output devices, mass storage media, or other suitable components for receiving, processing, storing, and communicating data. Both the input devices and output devices may include fixed or removable storage media such as a magnetic computer disk, CD-ROM, or other suitable media operable to both receive input from and provide output to a user of user system 520. Additionally, the user system 520 may include any suitable combination of software, firmware, and hardware. As previously noted, the various features and aspects as previously described with respect to the methods of the disclosed subject matter likewise can be incorporated in the systems herein.

The disclosed subject matter is not to be limited in scope by the specific embodiments described herein. Indeed, various modifications of the disclosed subject matter in addition to those described herein will become apparent to those skilled in the art from the foregoing description and the accompanying figures. Such modifications therefore fall within the scope of the appended claims.

What is claimed is:

1. A method of managing patient healthcare, comprising:
creating a patient profile including patient data for a patient;
screening the patient for a disease based on the patient profile;
identifying at least one test to assess a state of the disease based on the patient profile;
assessing the state of the disease based upon results of the test, and updating the patient profile to include the results of the at least one test and the assessed disease state;
determining a health management status of the patient indicative of a corresponding level of care based on progression of the disease, wherein the health management status is determined using a computer based on a comparison of the updated patient profile to predefined criteria regarding progression of the disease including a combination of a stage of the disease as established by professional guidelines and at least one additional indicator characteristic of a patient population corresponding to the patient; and
providing a recommended action based on the health management status and updated patient profile.

2. The method of claim 1, wherein the patient data includes at least one of the patient's age, weight, gender, ethnicity, diet, lifestyle habits, or pregnancy status.

3. The method of claim 1, wherein the patient data further includes prior medical records or history of medical conditions.

4. The method of claim 1, wherein the patient data further includes information of the patient's consanguine family members relevant to the disease.

5. The method of claim 1, wherein screening includes performing at least one screening test and including results of the at least one screening test in the patient profile.

6. The method of claim 5, wherein the at least one screening test is selected based on the patient data.

7. The method of claim 1, wherein screening is based on the professional guidelines relating to the disease.

8. The method of claim 1, wherein screening includes an evaluation of risk factors in the patient data relevant to the disease.

9. The method of claim 1, wherein the at least one test for assessing the state of the disease includes at least one diagnostic test.

10. The method of claim 9, wherein the at least one diagnostic test includes lab test or physical examination.

11. The method of claim 9, wherein the at least one diagnostic test is selected according to the professional guidelines relating to the disease.

12. The method of claim 1, wherein the disease for assessment is selected from diseases the patient is prone to have based on the patient profile.

13. The method of claim 1, wherein the disease for assessment is preselected.

14. The method of claim 1, wherein the disease is one of an autoimmune disease, an oncological disease, a pulmonary disease, a neurological disease, a metabolic disease, an infectious disease, a neurodegenerative disease, cardiovascular disease, diabetes, a chronic lower respiratory disease, pneumonia, and renal disease.

15. The method of claim 1, wherein the stage of the disease includes different types of the disease.

16. The method of claim 15, wherein the disease is diabetes, and the types of diabetes include gestational DM, DM Type 1, DM Type 2 diabetes.

17. The method of claim 15, wherein the disease is cardiovascular disease, and the types of the cardiovascular diseases include vascular disease and coronary artery disease.

18. The method of claim 1, further comprising
determining a health management status of the patient with respect to a second disease based on the updated patient profile and co-morbidity of the first disease with the second disease.

19. The method of claim 18, wherein the first disease and the second disease are selected from a cardiovascular disease and diabetes.

20. The method of claim 1, further comprising selecting whether the recommended action is provided to a recipient selected from a patient, a physician, a caregiver, a health care provider, a counselor or a financer.

21. The method of claim 20, wherein the recommended action is based upon the recipient.

22. The method of claim 1, wherein the recommended action includes using a beneficial agent, using a medical device, using a nutritional product, using a medical procedure, using a diagnostic test, obtaining related education, altering the patient's diet, or modifying the patient's lifestyle.

23. The method of claim 1, wherein the recommended action includes identifying where the patient can seek related products, treatment, procedures, tests, education or counseling.

24. The method of claim 1, wherein the recommended action is further based on the professional guidelines relating to the disease.

25. The method of claim 1, wherein the professional guidelines include guidelines published by the American Heart Association, American College of Cardiology, or American Stroke Association.

26. The method of claim 1, wherein the professional guidelines include guidelines published by American Diabetes Association.

27. The method of claim 1, wherein the recommended action is provided to a recipient on an internet-based system.

28. The method of claim 1, wherein the recommended action is displayed on a computer display.

29. The method of claim 1, wherein the recommended action includes providing transition services to the patient.

30. The method of claim 1, further comprising implementing the recommended action to address the disease.

31. A system for patient healthcare assessment and management, comprising:
at least one memory unit to store a patient profile including patient data and test results;
at least one processing unit operably coupled with the at least one memory unit, the at least one processing unit operable to:
screen a patient for a disease based on the patient profile,
identify at least one test to assess a state of the disease based on the patient profile,
assess the state of the disease based upon results of the at least one test, and update the patient profile to include the results of the at least one test and the assessed disease state,
determine a health management status of the patient indicative of a corresponding level of care based on progression of the disease, wherein the health management status is determined based on a comparison of the updated patient profile to predefined criteria regarding progression of the disease including a combination of a stage of the disease as established by professional guidelines and at least one additional indicator characteristic of a patient population corresponding to the patient, and
provide a recommended action based on the health management status and the updated patient profile; and
a display operably coupled to the processing unit to display the recommended action for a recipient.

32. The system of claim 31, wherein the system is internet-based, and the recommended action is presented on an internet-enabled display device.

33. The system of claim 31, wherein patient data for the patient profile is retrieved from a database externally linked to the system.

34. The system of claim 31, the at least one processing unit further operable to:
determine a health management status of the patient with respect to a second disease based on the updated patient profile and co-morbidity of the first disease with the second disease.

35. The system of claim 34, wherein the first disease and the second disease are selected from a cardiovascular disease and diabetes.

* * * * *